US00PP22025P2

(12) United States Plant Patent
Iie

(10) Patent No.: US PP22,025 P2
(45) Date of Patent: Jul. 12, 2011

(54) ***HYDRANGEA* PLANT NAMED 'PEACE'**

(50) Latin Name: *Hydrangea macrophylla*
Varietal Denomination: PEACE

(76) Inventor: Ryoji Iie, Kyoto (JP)

( * ) Notice: Subject to any disclaimer, the term of this patent is extended or adjusted under 35 U.S.C. 154(b) by 0 days.

(21) Appl. No.: 12/658,301

(22) Filed: Feb. 10, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — Kent L Bell
(74) *Attorney, Agent, or Firm* — Penny J. Aguirre

(57) ABSTRACT

A new cultivar of *Hydrangea macrophylla* named 'PEACE' that is characterized by its free-flowering and reblooming habit, its well-developed mop-head type inflorescences comprised of double sterile flowers that are white in color, and its strong stems that resist rain and wind damage.

2 Drawing Sheets

Genus/species: *Hydrangea macrophylla.*
Varietal denomination: 'PEACE'.

BACKGROUND OF THE INVENTION

The present invention relates to a new and distinct cultivar of *Hydrangea macrophylla* and will be referred to hereafter by its cultivar name, 'PEACE'. 'PEACE' represents a new bigleaf *hydrangea*, a deciduous shrub grown for landscape use and for use as for use as a cut flower.

'PEACE' was derived from an ongoing controlled breeding program by the Inventor that focuses on developing new cultivars of bigleaf *hydrangeas* with unique flower colors and double flowers. 'PEACE' originated from a cross conducted in the Inventor's trial garden in June 1996 in Kyoto, Japan between an unnamed plant of *Hydrangea macrophylla* as the female parent and *Hydrangea macrophylla* 'Yamaajisai' (not patented) as the male parent. The new *Hydrangea* was selected as a unique single plant from the progeny of the cross in 2000.

Asexual reproduction of the new cultivar was first accomplished by softwood stem cuttings in Kyoto, Japan in 2000 by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'PEACE' as a unique cultivar of *Hydrangea macrophylla.*

1. 'PEACE' exhibits double sterile flowers that are white in color.
2. 'PEACE' exhibits a free flowering and repeating blooming habit; blooming from early April through early October in The Netherlands.
3. 'PEACE' exhibits well-developed mop-head type inflorescences.
4. 'PEACE' exhibits strong stems that are resistant to rain and wind damage.
5. 'PEACE' is sterile as the fertile flowers do not develop.

'PEACE' can be compared to its male parent, 'Yamaajisai', which differs from 'PEACE' in having smaller flowers that are pinkish in color, in having a flatter formed inflorescence, and in having weaker stems. There are no cultivars of *Hydrangea macrophylla* known to the Inventor that are similar to 'PEACE'. 'PEACE' can be compared to the cultivar 'Hanabi' (syn. 'Sumida-no-hanabi', not patented). 'Hanabi' exhibits white double flowers, however 'Hanabi' differs from 'PEACE' in having lace-cap type inflorescences on cascading stems.

BRIEF DESCRIPTION OF THE DRAWINGS

The photographs in the figures were taken of a two year-old plant of 'PEACE' as grown under greenhouse conditions with ambient light in a 3-liter container in Leimuiden, The Netherlands.

The photograph in FIG. 1 illustrates a side view of a single stem of 'PEACE' in full bloom.

Figure 1:
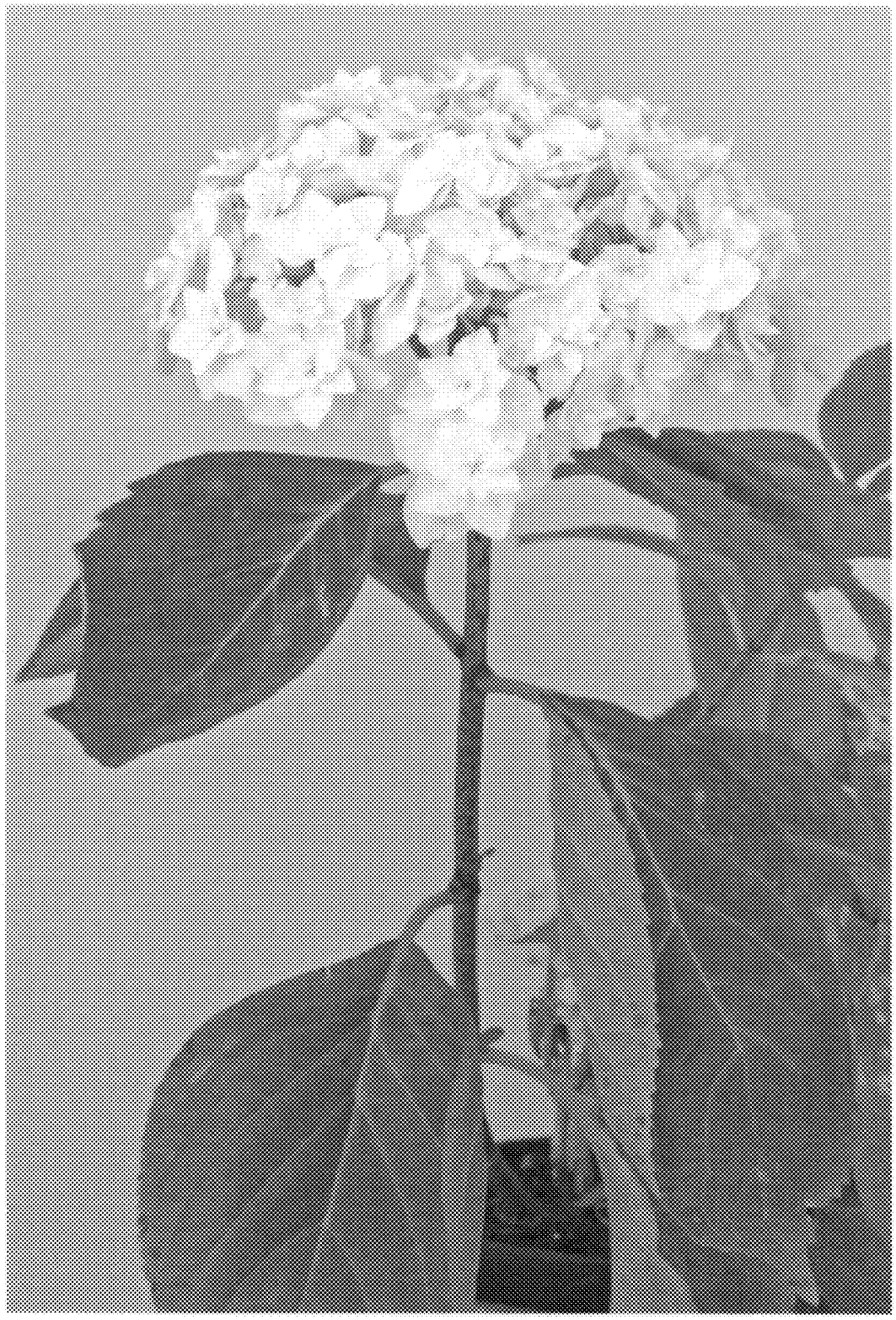
Figure 2:
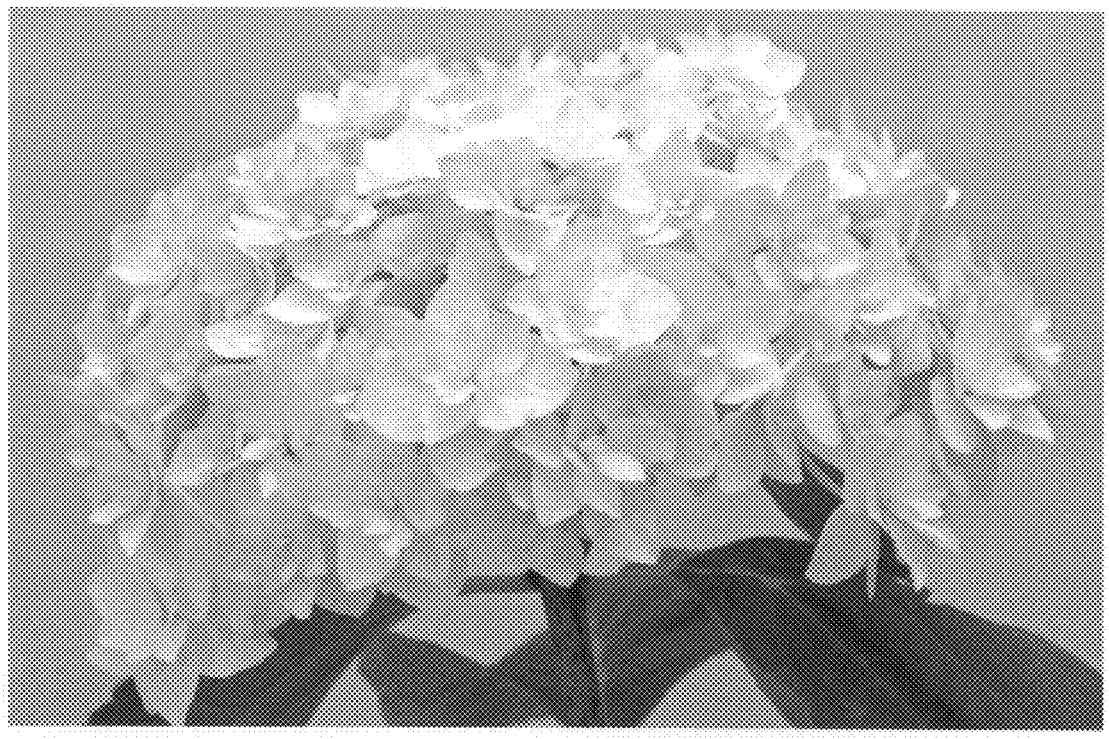

The photograph in FIG. 2 provides a close-up view of an inflorescence of 'PEACE'.

Figure 3:
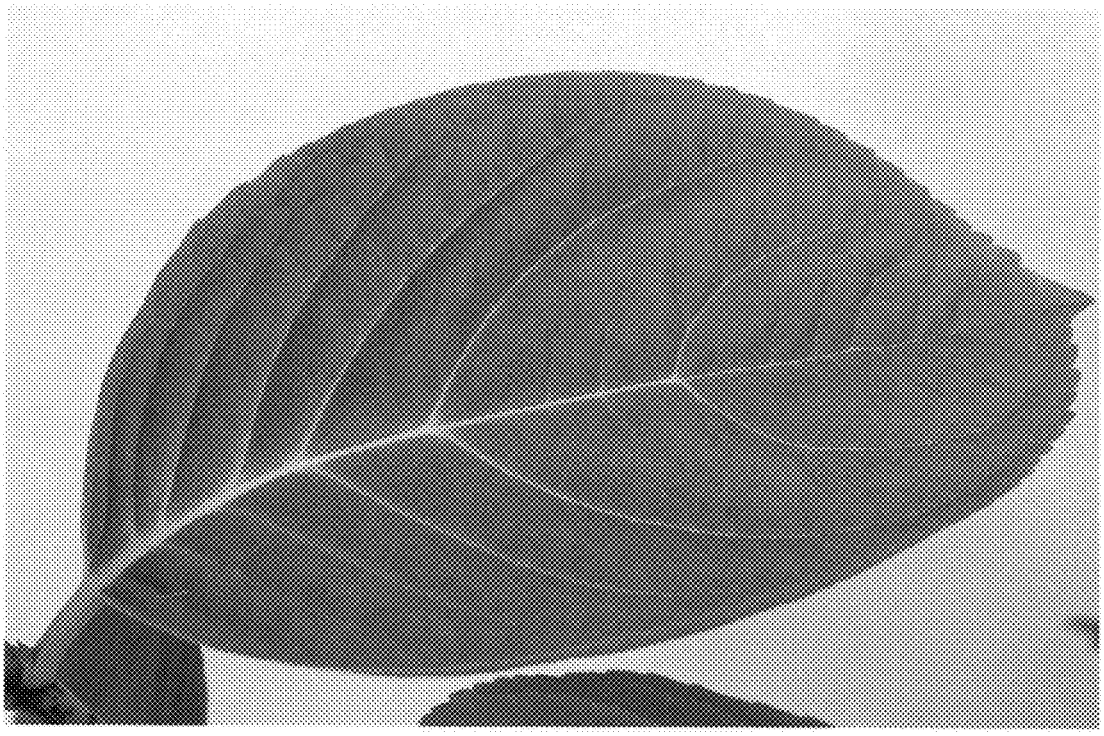

The photograph in FIG. 3 provides a close-up view of a leaf of 'PEACE'.

The colors in the photographs are as close as possible with the digital photography and printing techniques utilized and the color codes in the detailed botanical description more accurately describe the new *Hydrangea.*

BOTANICAL DESCRIPTION OF THE PLANT

The following is a detailed description of two year-old plants of 'PEACE' as grown under greenhouse conditions with ambient light in 4-liter containers in De Kwakel, The Netherlands. The plants were grown under average day temperatures of 12° C. to 22° C. and average night temperatures of 8° C. to 18° C. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—Continuously from early April through October in The Netherlands.

*Plant habit.*—Broadly upright, deciduous shrub, sturdy.

*Height and spread.*—Reaches about 32.8 cm in height and 72.4 cm in width.

*Hardiness.*—At least in U.S.D.A. Zones 5 to 9.

*Diseases resistance.*—No susceptibility or resistance diseases known to effect *H. macrophylla* has been observed.

*Root description.*—Fibrous, dense.

Growth and propagation:

*Propagation.*—Softwood stem cuttings.

*Time required for root initiation.*—About 4 weeks at an average temperature of 18° C. (night)/20° C. (day).

*Time required for root development.*—About 3 months to fully develop as a young plant when grown under greenhouse conditions at an average temperature of 18° C. (night)/20° C. (day).

*Time required to produce a salable crop.*—About 12 months from propagation to a flowering plant.

*Growth rate and vigor.*—Moderate.

Stem description:

*Stem shape.*—Round.

*Stem strength.*—Strong.

*Stem color.*—Immature; 144B, densely covered with lenticels that are an average of 2 mm in length and 0.5 mm in width, 9 per sq cm, and 187A in color, mature; 199A to 199B in color.

*Stem size.*—Average of 26.1 cm (to base of inflorescence) and average of 5 mm in width.

*Stem surface.*—Glabrous, semi-glossy.

*Branching.*—A single dormant stem will produce an average of 10 lateral branches, sublateral branching is determined by pinching; 2 stems develop per pinched node.

*Internode length.*—Average of 5.6 cm.

Foliage description:

*Leaf shape.*—Broad oval.

*Leaf arrangement.*—Opposite.

*Leaf division.*—Simple.

*Leaf number.*—Average of 8 (4 pairs) per lateral branch.

*Leaf base.*—Attenuate.

*Leaf apex.*—Acuminate.

*Leaf margins.*—Serrated.

*Leaf venation.*—Pinnate, color 145A to 145B.

*Leaf size.*—Average of 15 cm in length and 10.3 cm in width.

*Leaf attachment.*—Petiolate.

*Leaf surface.*—Smooth, slightly glossy.

*Leaf color.*—Young foliage upper surface; 141A to 143A, young foliage lower surface; 143A, mature foliage upper surface; 137A, mature foliage lower surface; 138A.

*Petioles.*—Average of 2 cm in length and 3.5 mm in width, 144B in color, surface is smooth and slightly glossy.

Inflorescence description:

*Inflorescence type.*—Terminal compound slightly flattened globose corymb of double rotate-shaped sterile flowers above fertile flower buds that do not develop.

*Lastingness of inflorescence.*—Persistent with color lasting about 4 weeks.

*Inflorescence number.*—One per lateral or sublateral stem if pinched.

*Inflorescence size.*—Average of 12.1 cm in height and 19.4 cm in diameter.

*Flower number.*—An average of 270 sterile flowers and 50 fertile flower buds per inflorescence.

*Flower durability to stress.*—High resistance to damage from high winds and rain.

*Flower fragrance.*—None.

*Flower aspect.*—Upright to outward on upright held inflorescences.

*Flower size.*—Sterile flowers; average of 3.5 cm in diameter and 1.6 cm in depth, fertile flowers; drop as buds and do not open.

*Flower buds.*—Sterile flowers; an average of 6 mm in length and 1 cm in width, ovate in shape, 150D in color, fertile flowers; an average of 2 mm in length and 2 mm in width prior to opening, globular in shape, 143B in color.

*Peduncles.*—Average of 8.9 cm in length and 3 mm in width, held at about a 30° angle to vertical, strong, 145A in color and speckled with 187A.

*Pedicels.*—An average of 2.5 cm in length and 1 mm in width, held at an average angle of 30° to vertical on sterile flowers and 10° on fertile buds, 63C in color, surface is glabrous and semi-glossy, moderate strength.

*Petals.*—Sterile flowers; not present, only sepals, fertile flowers; not present as buds drop after formation.

*Sepals.*—Sterile flowers; average of 14, rotate in arrangement, glabrous and dull surface (both surfaces), rhomboidal to narrowly elliptic in shape, margin is entire, an average of 1.4 cm in length and 9 mm in width, color when opening, upper surface and lower surface; 150D, color upper when fully open, upper surface and lower surface; NN155B and slightly tinged with 69D.

Reproductive organs:

*Presence.*—None present, absent on sterile flowers and fertile flowers abort at bud stage.

*Fruit and seed.*—None formed.

It is claimed:

1. A new and distinct cultivar of *Hydrangea* plant named 'PEACE' substantially as herein illustrated and described.

* * * * *